(12) United States Patent
Brudnak et al.

(10) Patent No.: US 9,476,084 B2
(45) Date of Patent: Oct. 25, 2016

(54) MICROORGANISM ENUMERATION METHODS

(71) Applicant: MAK Wood, Inc., Grafton, WI (US)

(72) Inventors: Mark A. Brudnak, Grafton, WI (US); Eric J. Baer, Grafton, WI (US)

(73) Assignee: MAK WOOD, INC., Grafton, WI (US)

( * ) Notice: Subject to any disclaimer, the term of this patent is extended or adjusted under 35 U.S.C. 154(b) by 0 days.

(21) Appl. No.: 14/684,049

(22) Filed: Apr. 10, 2015

(65) Prior Publication Data

US 2015/0291994 A1 Oct. 15, 2015

Related U.S. Application Data

(60) Provisional application No. 61/977,998, filed on Apr. 10, 2014.

(51) Int. Cl.
*C12Q 1/06* (2006.01)
*C12Q 1/08* (2006.01)

(52) U.S. Cl.
CPC .. *C12Q 1/06* (2013.01); *C12Q 1/08* (2013.01)

(58) Field of Classification Search
None
See application file for complete search history.

(56) References Cited

U.S. PATENT DOCUMENTS

2012/0263826 A1* 10/2012 Fang ............... A23L 1/0029
426/61
2013/0224303 A1* 8/2013 Nag ................ A23L 1/0029
424/490

OTHER PUBLICATIONS

Kim, K. et al. Effects of Rehydration Media and Immobilization in Ca-Alginate . . . Korean J Dairy Science 18(3)193-198, 1996.*
Standard Methods for the Examination of Dairy Products, Edited by Marshall, 16th Edition, 1992, Chapter 6, pp. 213-246.
Standard Methods for the Examination of Dairy Products, Edited by Wehr and Frank, 17th Edition, 2004.

* cited by examiner

*Primary Examiner* — Ralph Gitomer
(74) *Attorney, Agent, or Firm* — Michael Best & Friedrich LLP

(57) ABSTRACT

This disclosure provides methods for enumeration of microorganisms within a freeze-dried powder suspected of containing Lactobacilli or Bifidobacteria.

11 Claims, 1 Drawing Sheet

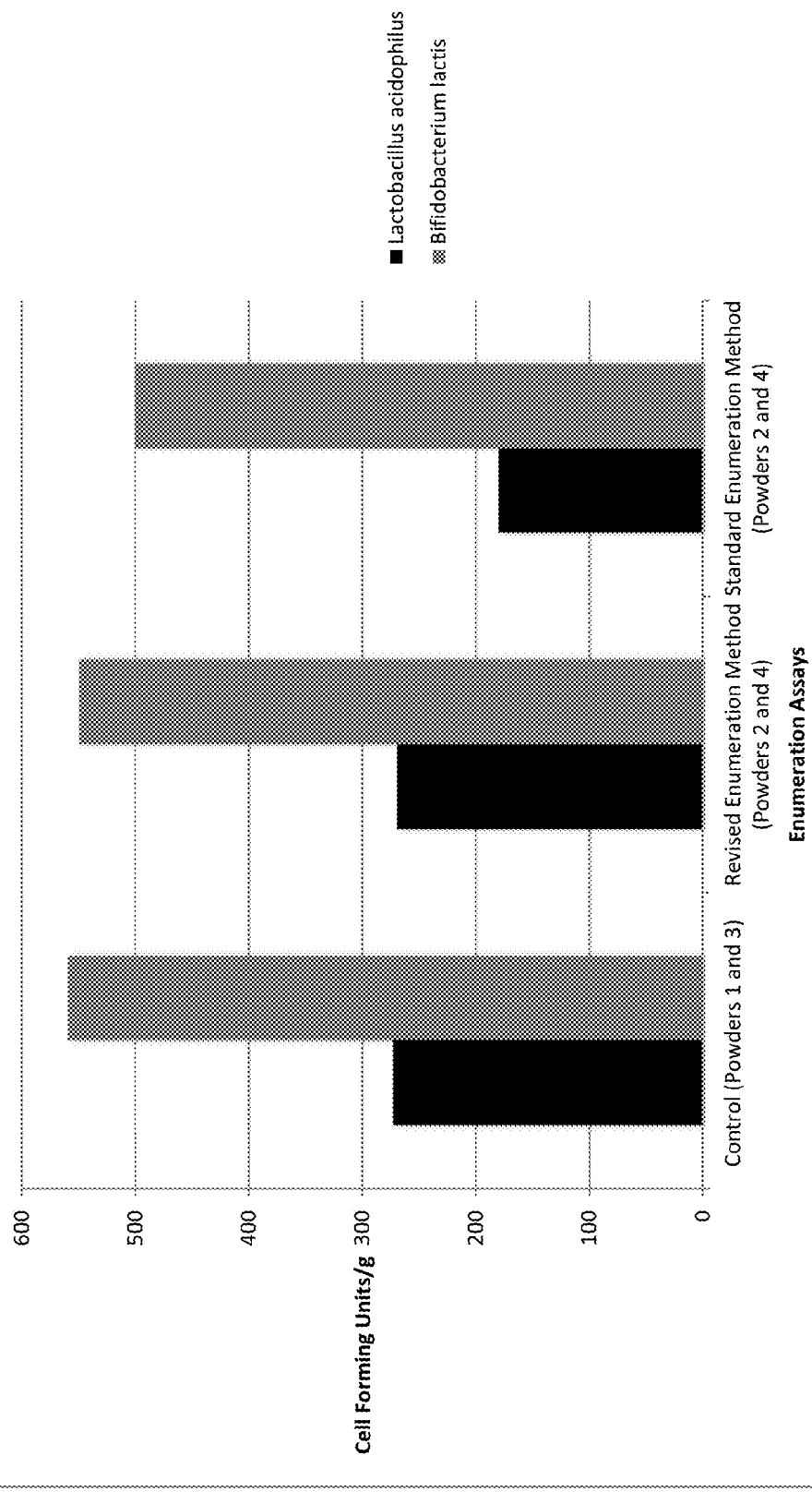

MICROORGANISM ENUMERATION METHODS

This application claims benefit of priority to provisional application 61/977,998 filed Apr. 10, 2014.

BACKGROUND

This disclosure provides improved methods for enumeration of lactic acid bacteria, such as Lactobacilli or Bifidobacteria, within a freeze-dried powder. In conventional enumeration methods, powdered lactic acid bacteria, which optimally grows under acidic conditions, is rehydrated in a culture broth having an acidic pH (e.g., Difco® MRS) to form a rehydrated sample. The sample is held at room temperature for 30 minutes, and is then serially diluted to form a series of serial dilutions. The serial dilutions are then plated with an agar composition to form a series of plates, which are incubated under anaerobic conditions for 72 hours to form colonies. Excessive incubation time may cause excessive radial growth of the colonies, such that the colonies grow into one another making them difficult to count. After incubation, the colonies on each plate are counted, and the number of microorganisms in the powder is quantified based on a correlation between the number of colonies and the dilution for each plate.

Some freeze-dried lactic acid powders may contain additional components, such as polymeric materials (e.g., alginate) that may delay the release of the microorganisms in certain environments. It has been unexpectedly found that the use of conventional methods for enumeration of microorganisms may be inaccurate when the powder contains these polymeric materials. Without wishing to be bound by theory, it is possible that the polymeric materials may lead to the agglomeration of colony forming units (CFUs) when the powder is reconstituted, diluted and plated, thereby leading to an undercounting of viable microorganisms. For example, if a sample having CFUs contains a polymeric material in sufficient quantity to cause CFUs to be bound to other CFUs at the time of plating, then conventional methods may undercount the actual number of CFUs. Accordingly, a need exists for improved enumeration methods that overcome the aforementioned shortcomings.

SUMMARY

This disclosure provides methods for enumeration of microorganisms within a freeze-dried powder suspected of containing Lactobacilli or Bifidobacteria. The methods may comprise rehydrating the powder with a culture broth having a pH between about 7.0 and about 8.5 to form a rehydrated sample, holding the sample at a temperature between about 10° C. and about 35° C. for a length of time of about 20 minutes to about 60 minutes, serially diluting the sample to form a plurality of serial dilutions, plating each serial dilution with an agar composition comprising cysteine hydrochloride in an amount of about 0.005% to about 0.5% by weight/volume percent of the agar composition to form a plurality of plates, incubating the plates, counting the colonies in each plate, and quantifying the microorganisms in the powder based on a correlation between the number of colonies and the dilution for each plate.

BRIEF DESCRIPTION OF THE DRAWINGS

FIG. 1 is a bar chart comparing the enumeration method of the present disclosure with a standard enumeration method.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "about" is intended to encompass the value that the term is modifying plus or minus an amount that a person having ordinary skill in the art would identify as accounting for user error, instrumental error, or a combination of user and instrumental error.

This disclosure provides methods for enumeration of microorganisms within a freeze-dried powder suspected of containing Lactobacilli or Bifidobacteria. The methods may comprise rehydrating the powder with a culture broth having a pH between about 7.0 and about 8.5 to form a rehydrated sample, holding the sample at a temperature between about 10° C. and about 35° C. for a length of time of about 20 minutes to about 60 minutes, serially diluting the sample to form a plurality of serial dilutions, plating each serial dilution with an agar composition comprising cysteine hydrochloride in an amount of about 0.005% to about 0.5% by weight/volume percent of the agar composition to form a plurality of plates, incubating the plates, counting the colonies in each plate, and quantifying the microorganisms in the powder based on a correlation between the number of colonies and the dilution for each plate. One or more (e.g., all) of the steps of the process may be aseptic.

I. Rehydrating

As indicated above, powder containing lactic acid bacteria (e.g., Lactobacilli or Bifidobacteria) may be rehydrated with a culture broth having a pH between about 7.0 and about 8.5 to form a rehydrated sample. In some embodiments, the powder may comprise a polymeric material, such as alginate. It has been surprisingly determined (See Example) that rehydrating powders containing polymeric materials, such as alginate, with a culture broth having a slightly basic pH (i.e., between about 7.0 and 8.5) allows for a far more accurate determination of the number of microorganisms in the powder, despite the fact that lactic acid bacteria grow better under acidic conditions.

The culture broth may include any broth now known or hereinafter devised for the cultivation of lactic acid bacteria, including, but not limited to, Lactobacilli MRS Broth (based on the formulations of deMan, Rogosa and Sharpe) adjusted to a pH between about 7.0 and about 8.5. In some embodiments, the culture broth may have a pH between about 7.2 and about 7.8, such as a pH of about 7.5. The reconstituting step may include contacting the powder with sterile MRS broth, and blending the powder and broth (e.g., in a stomacher) to form the sample.

II. Holding

The sample may be held at a temperature between about 10° C. and about 35° C. for a length of time of about 20 minutes to about 60 minutes.

For example, the sample may be held at a temperature of at least about 10° C., at least about 11° C., at least about 12° C., at least about 13° C., at least about 14° C., at least about 15° C., at least about 16° C., at least about 17° C., at least about 18° C., at least about 19° C., at least about 20° C., at least about 21° C., at least about 22° C., at least about 23° C., at least about 24° C., at least about 25° C., at least about 26° C., at least about 27° C., at least about 28° C., at least about 29° C., at least about 30° C., at least about 31° C., at least about 32° C. or at least about 33° C. The methods may comprise holding the sample at a temperature of at most about 35° C., at most about 34° C., at most about 33° C., at most about 32° C., at most about 31° C., at most about 30° C., at most about 29° C., at most about 28° C., at most about 27° C., at most about 26° C., at most about 25° C., at most about 24° C., at most about 23° C., at most about 22° C., at most about 21° C., at most about 20° C., at most about 19° C., at most about 18° C., at most about 17° C., at most about 16° C., at most about 15° C., at most about 14° C., at most about 13° C., or at most about 12° C. This includes, but is not limited to, embodiments where the sample is held at a temperature between about 10° C. and about 35° C., between about 15° C. and about 30° C., and between about 20° C. and about 23.5° C.

The sample may be held at a temperature disclosed above for at least about 20 minutes, such as at least about 25 minutes, at least about 30 minutes, at least about 35 minutes, at least about 40 minutes, at least about 45 minutes, or at least about 50 minutes. The sample may be held at a temperature disclosed above for at most about 60 minutes, such as at most about 55 minutes, at most about 50 minutes, at most about 45 minutes, at most about 40 minutes, at most about 35 minutes, or at most about 30 minutes. This includes embodiments where the sample is held at a temperature disclosed above for between about 20 minutes to about 60 minutes, such as between about 25 minutes and about 55 minutes, or between about 20 minutes and about 40 minutes. In certain embodiments, the sample may be held at a temperature disclosed above for 30 minutes.

In some methods, the sample may be blended (e.g., in a stomacher) after holding the sample.

III. Serially Diluting

The methods may comprise serially diluting the sample to form a plurality (e.g., a series) of serial dilutions. Serially diluting the sample may comprise diluting the sample to form a primary dilution, and diluting the primary dilution to form one or more secondary dilutions. The serial dilutions may be made using a variety of diluents for facilitating plating of microorganisms on an agar plate. Any suitable diluent may be used, including those now known or herein after devised. Suitable diluents include, but are not limited to 0.1% peptide dilution blanks. The serial dilutions each have a pH between about 7.0 and about 8.5, such as a pH between about 7.2 and about 7.8. In some embodiments, the serial dilutions each may have a pH of about 7.5.

IV. Plating and Incubating the Plates

Plating may be performed by conventional plating methods known to a person having ordinary skill in the art, so long as the plating methods do not encumber the other steps in the method. In some embodiments, the methods may comprise plating the serial dilutions with an agar composition comprising cysteine hydrochloride in an amount from about 0.005% to about 0.5% by weight/volume percent of the agar composition to form plates. The agar composition may comprise a MRS agar (based on the formulations of deMan, Rogosa and Sharpe).

The plates may be incubated according to conventional methods known to a person having ordinary skill in the art, so long as the incubating methods do not encumber the other steps in the method. The plates may be incubated at a temperature between about 30° C. and about 45° C. for a length of time between about 90 hours and about 130 hours. This length of incubation differs from conventional methods, in that incubation for these lengths of time would lead to excessive radial growth of colonies under conventional methods, thus making it difficult, if not impossible, to count the number of colonies. In certain embodiments, the incubating step may be performed under anaerobic conditions.

V. Counting and Quantifying

In principle, the counting and quantifying steps may be performed by conventional counting and quantifying methods known to those of ordinary skill in the art, so long as the counting methods do not encumber the other steps in the method. In some embodiments, counting colonies may comprise counting colonies only on plates having between about 25 and about 250 colonies.

EXAMPLES

The following examples are presented to illustrate the present invention, and are not intended in any way to otherwise limit the scope of the invention.

Example 1

The number of cell forming units contained in samples of freeze-dried *Lactobacillus acidophilus* and *Bifidobacterium lactis* powders were analyzed using the following standard and revised enumeration methods.

Standard Method

1. Aseptically weigh 11 grams of the dried powder into a sterile stomacher bag.

2. Aseptically add 99 mL of sterile, room temperature, Difco MRS broth (pH of Difco MRS broth is acidic pH of 6.5) to the 11 grams of dried powder in the stomacher bag.

3. Turn stomacher on and allow to blend for 30 seconds.

4. Hold the sample at room temperature for 30 minutes to rehydrate the freeze-dried powder.

5. Return the sample to the stomacher and blend for an additional 30 seconds.

6. Make serial dilutions in 99 mL 0.1% peptone dilution blanks by adding 1 mL of the primary $10^{-1}$ dilution (from the stomacher bag) to 99 mL of diluent with a 1 mL pipette so as to obtain a $10^{-3}$ dilution. Repeat this operation until the desired dilution series is obtained. Shake dilution bottles as directed in *Standard Methods for the Examination of Dairy Products*.

7. Proceeding in triplicate, transfer 1 mL of each appropriate dilution to labeled, sterile Petri plates with sterile 1 mL pipettes.

8. Take a bottle of sterile Difco MRS agar that has been melted (100° C. for 30 mins.) and tempered to 45° C. in a 45° C. water bath and sanitize the bottle by dipping it into a 200 PPM chlorine solution (made fresh daily), or by flaming the lip of the bottle.

9. Under a laminar hood, aseptically add 1 mL of sterile 5% cysteine-HCl solution to each 100 mL of the Difco MRS agar to achieve a final cysteine-HCl concentration of 0.05% in the MRS agar.

10. Pour approximately 15 mL of the MRS/0.05% cysteine-HCl agar into each plate. Swirl the plates to mix, and let solidify at room temperature on a cool level surface.

11. Plates need to be under anaerobic conditions (BD GasPak EZ Container Systems with indicator in anaerobic jar) within one hour of their being poured. Incubate at 38° C. for 72 hours.

12. Count colonies on the MRS/0.05% cysteine-HCl agar plates and record as viable *Bifidobacterium* and Lactobacilli cell count per gram, taking into account the dilution factors of the plates counted. Only plates having between 25 and 250 colonies should be counted.

Revised Method

1. Aseptically add 99 mL of sterile, room temperature, Difco MRS broth (pH adjusted to a basic pH of 7.5) to 1 gram of dried powder in a sterile stomacher bag.

2. Turn stomacher on and blend for 30 seconds.

4. Hold the sample at room temperature for 30 minutes to rehydrate the freeze-dried powder.

5. Return the sample to the stomacher and blend for an additional 30 seconds.

6. Make serial dilutions in 9 mL 0.1% peptone dilution blanks (pH adjusted to 7.5) by adding 1 mL of the primary $10^{-2}$ dilution (from the stomacher bag) to 9 mL of diluent with a 1 mL pipette so as to obtain a $10^{-3}$ dilution, rinse the pipette three times. Repeat this operation until the desired dilution series is obtained. Shake dilution bottles as directed in *Standard Methods for the Examination of Dairy Products*.

7. Proceeding in triplicate, transfer 1 mL of each appropriate dilution to labeled, sterile Petri plates with sterile 1 mL pipettes.

8. Take a bottle of sterile Difco MRS agar that has been melted (100° C. for 30 mins.) and tempered to 45° C. in a 45° C. water bath and sanitize the bottle by dipping it into a 200 PPM chlorine solution (made fresh daily), or by flaming the lip of the bottle.

9. Under a laminar hood, aseptically add 1 mL of sterile 5% cysteine-HCl solution to each 100 mL of the Difco MRS agar to achieve a final cysteine-HCl concentration of 0.05% in the MRS agar, swirl bottle to mix MRS with cysteine-HCL.

10. Pour approximately 15 mL of the MRS/0.05% cysteine-HCl agar into each plate. Swirl the plates to mix, and let solidify at room temperature on a cool level surface.

11. Plates need to be under anaerobic conditions (BD GasPak EZ Container Systems with indicator in anaerobic jar) within one hour of their being poured. Incubate at 38° C. for 96 hours.

12. Count colonies on the MRS/0.05% cysteine-HCl agar plates and record as viable cell count per gram, taking into account the dilution factors of the plates counted. Only plates having between 25 and 250 colonies should be counted.

Results

As shown in Table 1, freeze-dried *Lactobacillus acidophilus* powder (Powder 1) and *Bifidobacterium lactis* powder (Powder 3) each were also mixed with sodium alginate and salts (Powders 2 and 4, respectively). As a control, Powders 1 and 3 were analyzed using the standard enumeration method described above to quantify the number of cell forming units per gram of the freeze dried concentrates. Powders 2 and 4 (i.e., each containing alginate and salts) were then analyzed by both the standard and the revised enumeration methods described below to quantify the number of cell forming units per gram of the freeze dried concentrates used to make the powders. As shown in FIG. 1, when the revised enumeration method was used to quantify the cell forming units present in the freeze dried powder used to make Powders 2 and 4, the number agreed with the number calculated for the control. However, when the standard enumeration method was used to quantify the cell forming units present in the freeze dried powder used to make Powders 2 and 4, the number was substantially lower than the number calculated for the control, thus indicating that the standard enumeration method undercounts the total number of cell forming units when the powder is in the presence of alginate and salts.

TABLE 1

Powders analyzed using various methods.

| | Powder 1 (% by wt) | Powder 2 (% by wt) | Powder 3 (% by wt) | Powder 4 (% by wt) |
|---|---|---|---|---|
| Freeze Dried Concentrated *Lactobacillus acidophilus* | 100 | 70 | — | — |
| Freeze Dried Concentrated *Bifidobacterium lactis* | — | — | 100 | 70 |
| Sodium alginate | — | 25 | — | 25 |
| Tricalcium phosphate | — | 3.75 | — | 3.75 |
| Sodium chloride | — | 0.625 | — | 0.625 |
| Potassium chloride | — | 0.625 | — | 0.625 |

What is claimed is:

1. A method for enumeration of microorganisms within a freeze-dried powder suspected of containing Lactobacilli or Bifidobacteria, the method comprising:
   rehydrating the powder with an MRS culture broth having a pH between about 7.2 and about 8.5 to form a rehydrated sample, wherein the powder includes alginate;
   holding the sample at a temperature between about 10° C. and about 35° C. for a length of time of about 20 minutes to about 60 minutes;
   serially diluting the sample to form a plurality of serial dilutions, wherein the serial dilutions each have a pH between about 7.2 and about 8.5;
   plating each serial dilution with an agar composition comprising cysteine hydrochloride in an amount of about 0.005% to about 0.5% by weight/volume percent of the agar composition to form a plurality of plates;
   incubating the plates;
   counting the colonies in each plate; and
   quantifying the microorganisms in the powder based on a correlation between the number of colonies and the dilution for each plate.

2. The method of claim 1, wherein the culture broth has a pH between about 7.2 and about 7.8.

3. The method of claim 2, wherein the culture broth has a pH of about 7.5.

4. The method of claim 1, wherein the serial dilutions are made using 0.1% peptone dilution blanks.

5. The method of claim 4, wherein the serial dilutions each have a pH between about 7.2 and about 7.8.

6. The method of claim 5, wherein the serial dilutions each have a pH of about 7.5.

7. The method of claim 1, wherein the sample is held at a temperature between about 20° C. and about 23.5° C.

8. The method of claim 1, wherein the plates are incubated at a temperature between about 30° C. and about 45° C. for a length of time between about 90 hours and about 130 hours.

9. The method of claim 1, wherein the plates are incubated under anaerobic conditions.

10. The method of claim 1, wherein one or more steps are aseptic.

11. The method of claim 1, wherein the counting step comprises only counting the colonies on plates having between about 25 and about 250 colonies.

\* \* \* \* \*